United States Patent [19]

Konishi et al.

[11] Patent Number: 4,942,136

[45] Date of Patent: Jul. 17, 1990

[54] METHOD FOR PRODUCTION OF FLUORESCENCE-LABELED FAB'

[75] Inventors: Shohei Konishi; Akira Imai, both of Yokkaichi; Goro Wakabayashi, Suzuka; Hiroshi Kishioka, Yokkaichi, all of Japan

[73] Assignees: Agency of Industrial Science and Technology; Ministry of International Trade and Industry, Tokyo, Japan

[21] Appl. No.: 175,289

[22] Filed: Mar. 30, 1988

[30] Foreign Application Priority Data

Jul. 29, 1987 [JP] Japan .............................. 62-187648

[51] Int. Cl.$^5$ ........................................ G01N 33/563
[52] U.S. Cl. .................................. 436/512; 436/546; 436/547; 530/402; 530/404; 530/412; 530/417
[58] Field of Search ...................... 436/512, 546–547; 530/402, 404, 412, 417

[56] References Cited

U.S. PATENT DOCUMENTS 4,207,075  6/1980  Liburdy .............................. 436/547
4,258,130  3/1981  Ashton et al. ....................... 436/512

*Primary Examiner*—Robert J. Warden
*Assistant Examiner*—Lyle Alfandary-Alexander
*Attorney, Agent, or Firm*—Oblon, Spivak, McClelland, Maier & Neustadt

[57] ABSTRACT

A fluorescence-labeled Fab' is produced by causing a fluorescent substance to react with a Fab', dialyzing the resultant reaction solution, allowing the dialyzate to stand at rest thereby effecting reversion of unconjugated Fab' into F(ab')$_2$ and giving rise to a reaction solution containing a fluorescence-labeled Fab' and F(ab')$_2$ and collecting the fluorescence-labeled Fab' from the reaction solution.

13 Claims, No Drawings

METHOD FOR PRODUCTION OF FLUORESCENCE-LABELED FAB'

BACKGROUND OF THE INVENTION

1. Field of the Invention

This invention aims to provide a method for the production of a novel fluorescence-labeled Fab'. It, therefore, relates to the fields of determination, analysis, and clinical diagnosis.

2. Prior Art Statement

Antibodies labeled with fluorescent substances are used for detection of biologically active molecules in various vital tissues and for detection of antigens present in very low concentrations in body fluids.

For the production of fluorescence-labeled antibodies, fluorescent substances such as fluorescein isocyanate and derivatives thereof have been widely used. However, the fluorescence-labeled antibodies produced using these substances have decreased the activity of the antibodies because these substances are conjugated to the antibodies by the $NH_2$ group of the antibodies, which is the same part by which the antibodies bind to antigens.

As cases in which fluorescent substances reactive with the SH group have been used, there can be mentioned, for example, the production of fluorescence-labeled antibodies by the use of N-(7-dimethyl-4-aminomethylcumarinyl)maleimide disclosed in Japanese Published Unexamined Patent Application No. 55861/83 and that by the use of N-(3-pyrene)maleimide introduced by Robert P. Liburdy in Journal of Immunological Method, 28, (1979) pp. 233-242, for example. So far there has been no report relating to conjugation to the SH group of Fab'.

Similarly in the production of enzyme-labeled antibodies, enzymes are conjugated to antibodies through the medium of the $NH_2$ group of the antibodies by the glutaraldehyde method or the periodate method, for example. Again in this case, it is known that these methods of enzyme-labeled antibodies are apt to decrease the activity of the antibodies and induce non-specific reactions. Ishikawa et al. have solved this problem by a method which conjugates an enzyme to the SH group of a given antibody through the medium of a maleimide compound possessing a maleimide group, namely a method which conjugates the enzyme to a different part from that at which the antibody binds to an antigen, specifically to the hinge region of the antibody.

Antibodies have five types, which are IgG, IgA, IgM, IgD, and IgE. Among these, IgG can be easily separated from antiserum and collected in high yields. IgG is composed of two heavy chains (H chains) and two light chains (L chains) and has the shape of the letter Y. Each H chain is coupled to each L chain by a disulfide bond (-S—S-) and the two H chains are also coupled to each other by a disulfide bond. The disulfide bonds of an antibody are severed through reduction with a reducing agent, into two SH groups. When the disulfide bond between an H chain and an L chain is reduced, the site at which the antibody is bound to an antigen is split at the same time. To avoid this trouble, the disulfide bond between the two H chains must be selectively reduced. Selective conversion of the disulfide bond between the two H chains to SH groups can be attained by digesting a given antibody with pepsin thereby producing $F(ab')_2$ and subsequently reducing the $F(ab')_2$ under relatively mild conditions. Fab' is obtained by reducing $F(ab')_2$. The hinge region is where the disulfide bond between the two H chains to be reduced is located.

The maleimide group of a maleimide compound tends to conjugate itself to the SH group and, therefore, is conjugated easily to the SH group of the Fab'. The method proposed by Ishikawa et al. attains the enzyme-labeled Fab' by the maleimide method and, therefore, does not impair the antigen binding activity.

Peroxidase, a labeling enzyme generally used in the conjugation of an enzyme with the Fab' has a molecular weight of 40,000, and the Fab' has a molecular weight of 47,000. Thus, they have nearly equal molecular weights. The enzyme-labeled Fab', therefore, has a molecular weight about twice that of peroxidase or Fab'. Separation of the unconjugated Fab' from the reacted product is easily attained by gel filtration (molecular sieve) by virtue of the difference in molecular weight.

Some fluorescent substances react with the SH group. It is, therefore, easily inferred that the production of a fluorescence-labeled Fab' will be attained by causing such a fluorescent substance to be conjugated to the SH group of the Fab'. Since the molecular weight of such a fluorescent substance is about 1,000 at most, it has been difficult to separate the fluorescence-labeled Fab' (molecular weight about 48,000) and the unconjugated Fab' (molecular weight about 47,000) by virtue of the difference of molecular weight. All attempts to obtain a purified fluorescence-labeled Fab' product from reaction of the SH group of the Fab' have failed.

Therefore, only fluorescence-labeled Fab' including unconjugated Fab' have been obtainable. Their F/P values (the number of molecules of the fluorescent substance per molecule of the antibody) have been low and their fluorescence intensities have been weak.

OBJECT AND SUMMARY OF THE INVENTION

This invention relates to a method for the production of a fluorescence-labeled Fab' containing no unconjugated Fab', possessing a high F/P value, and emitting fluorescence of high intensity.

The $F(ab')_2$ by a treatment with a reducing agent, is split into two Fab's as the disulfide bond at the hinge region thereof is severed and converted into the SH group. When the reducing agent is removed and the Fab's are reverted to a neutral or acidic state, the two Fab's readily form a disulfide bond and convert into $F(ab')_2$. A liquid containing the Fab', therefore, incorporates therein EDTA (ethylene diamine tetraacetic acid) as an agent for precluding re-formation of the disulfide bond. The fluorescence-labeled Fab' produced by virtue of the SH group of the Fab' do not have the free SH group. When the reducing agent is removed and the fluorescence-labeled Fab' solution is reverted to the neutral or acidic state in the absence of EDTA, therefore, it is not allowed to revert to the $F(ab')_2$. On the basis of this, it has now been found that the fluorescence-labeled Fab' is obtained by causing a fluorescent substance to react with the Fab', then dialyzing the resultant reaction solution with a neutral or acidic buffer solution, allowing the reaction solution to stand at rest thereby reverting the unconjugated Fab' to the $F(ab')_2$ of a molecular weight of 94,000, and separating the $F(ab')_2$ through gel filtration.

DETAILED DESCRIPTION OF THE PREFERRED EMBODIMENTS

In accordance with the present invention, a fluorescence-labeled antibody is obtained by causing a fluorescent substance to react with Fab', dialyzing the resultant reaction solution, allowing the dialyzed reaction solution to stand at rest, and collecting the produced fluorescence-labeled Fab' from the solution obtained after the standing.

As the antibody for the production of the Fab', IgG is used. IgG is advantageous over the other types of antibodies (IgA, IgM, IgD, and IgE) in the point that it is marketed in a wider variety of types and is easily separated from antiserum and purified. Concrete examples of the human antigens which the commercially available antibodies are capable of discerning include α-fetoprotein, CEA, ferritin, $\beta_2$-microglobulin, $T_3$, $T_4$, TSH, HBs antigen, CRP, $C_3$, $C_4$, transferrin, FDP, IgG, IgA, and IgM.

As concrete examples of the fluorescent substance which is capable of reacting with the SH group, there can be cited 5-(iodoacetamidoethyl)aminonaphthalene-1-sulfonic acid, 5-iodoacetamide fluorescein, N-(1-anilinonaphtyl-4)maleimide, N-(7-dimethylamino-4-methylcumarinyl)maleimide, N-(1-pyrene)maleimide, N-(3-pyrene)maleimide, eosin-5-iodoacetamide, fluorescein mercury acetate, and 2-[4'(2''-iodoacetamide)-phenyl]-aminonaphthalene-6-sulfonic acid.

The production of the Fab' from the IgG is accomplished by first digesting the IgG with pepsin thereby preparing F(ab')$_2$ and splitting the F(ab')$_2$ with a reducing agent into Fab's. The preparation of the F(ab')2 from the IgG can be carried out by the method described in Immunochemistry in Practice, p. 53, published by Blackwell Scientific Publications (1982) or the method described in Menekikagaku (Immunochemistry), p. 108, published by Nakayama Shoten (1972).

Then, the F(ab')$_2$ prepared as described above is split into the Fab' with a reducing agent. This splitting is carried out by dialyzing the F(ab')$_2$ against a 2–5 mM EDTA-containing buffer solution (pH 6.5 to 8.5). As the buffer solution, tris-hydrochloride buffer solution (pH 8.0) or phosphate buffer solution (pH 8.0) may be used, for example. Then, the dialyzed F(ab')$_2$ solution is mixed with a reducing agent. As the reducing agent, 2-mercaptoethanol, 2-methylmercaptoethanol amine, or dithiothreitol may be used, for example. The F(ab')$_2$ concentration is adjusted so that the final concentration after addition of the reducing agent will fall in the range of 1 to 20 mg/ml, preferably 3 to 8 mg/ml. The amount of the reducing agent to be added is desired to be adjusted so that the final concentration thereof will fall in the range of 0.2 to 2.0 mM. The F(ab')$_2$ solution which has incorporated the reducing agent therein is incubated for under nitrogen at room temperature for a period of 0.5 to 1.5 hours, to complete the production of the Fab'. After completion of the incubation, the reaction solution is analyzed by high-performance liquid chromatography at a wavelength of 280 nm to confirm that the F(ab')$_2$ has been split into the Fab'.

The fluorescence-labeled Fab' is produced by causing a fluorescent substance to react with the Fab' obtained as described above. The Fab' solution is dialyzed against an EDTA-containing buffer solution (pH 6.0 to 8.0) to remove the used reducing agent. The Fab' solution thus freed of the reducing agent and the fluorescent substance added thereto are incubated under nitrogen at room temperature for about one hour. Desirably, the Fab' concentration during this reaction is in the range of 1 to 20 mg/ml, preferably 3 to 8 mg/ml. The concentration of the fluorescent substance is desired to be in the range of 0.1 to 1.0 mM, preferably 0.2 to 0.5 mM.

After completion of this reaction, the reaction solution is dialyzed against a buffer solution containing no EDTA (pH 5.0 to 7.0) at a temperature in the range of 2° to 10° C., preferably at 4° C., for a period in the range of 4 to 24 hours, preferably for 12 hours. Then, the dialyzed solution is left standing at a temperature in the range of 2° to 10° C., desirably at 4° C., for a period in the range of 24 to 72 hours, preferably for 48 hours. By the dialysis and the subsequent standing the unconjugated Fab' can be reverted to the F(ab')$_2$.

The separation of the fluorescence-labeled Fab' from the F(ab')$_2$ thus reverted from the unconjugated Fab' is effected by the use of a gel filtration column capable of separating molecules having molecular weights in the range of 10,000 to 100,000. To be concrete, by the use of a column packed with a gel (produced by Pharmacia Fine Chemical Corp. and marketed under the tradename "Sephadex G-150", "Sephadex G-200", "Sephacryl S-200", or "Sephacryl S-300"), the fluorescence-labeled Fab' antibody remaining after the elution of the F(ab')$_2$ resulting from the reversion of the unconjugated Fab' are recovered. Thus, the present invention permits production of a fluorescence-labeled Fab' antibody possessing a high F/P value and exhibiting a high intensity of fluorescence.

Now, the invention will be described more specifically below with reference to working examples.

EXAMPLE 1

3 ml of an IgG fraction of an anti-human IgG antiserum (9.8 mg/ml, produced by DAKO Company) was dialyzed against a 0.1M acetate buffer solution (pH 4.5) at 4° C. for three hours. 1.2 mg of pepsin (produced by Sigma Co.) was dissolved in the resultant dialyzate and the mixture was incubated at 37° C. for 16 hours. After incubation, the pH of the digested IgG solution was adjusted to 7 with an aqueous 1.0N sodium hydroxide solution and applied for purification of gel filtration to a column (2.5 cm in diameter and 100 cm in length) packed with Sephacryl S-200 (produced by Pharmacia Fine Chemical Corp.). The purified F(ab')$_2$ was freeze dried. Consequently 10 mg of an anti-human IgG•F(ab')$_2$ was obtained. As the buffer solution for the gel filtration, a 0.02M tris-hydrochloride buffer solution containing 2% of sodium chloride (pH 8.2) was used.

In 1.5 ml of 0.04M tris-hydrochloride buffer solution containing 5 mM of EDTA (pH 8.0), 10 mg of the anti-human IgG•F(ab')$_2$ was dissolved. 0.075 ml of 2-mercaptoethanol (produced by Wako Junyaku K.K.) dfiluted with distilled water to the concentration 0.1M was added to the anti-human IgG•F(ab')$_2$ solution. The mixture was incubated under nitrogen at room temperature for 45 minutes, to afford an anti-human IgG•Fab'. This antihuman IgG•Fab' solution was dialyzed against 0.1M phosphate buffer solution containing 5 mM of EDTA (pH 8.0) at 4° C. for two hours. After completion of the dialysis, the resultant dialyzate and 375 μl of a 1.7 mM N-(1-pyrene)maleimide dissolved in acetone were left reacting under nitrogen at room temperature for one hour, to conjugate the fluorescence substance, N-(1-pyrene)maleimide, to the anti-human IgG•Fab'.

The reaction solution was dialyzed against 0.1M phosphate buffer solution (pH 7.0) at 4° C. for 12 hours and then left standing at rest at 4° C. for 48 hours.

A sample (sample A) was sampled immediately after the conjugated reaction. A sample (sample B) was sampled after the process of dialysis and a sample (sample C) was sampled after 48 hour's standing. The three samples were analyzed by high-performance liquid chromatography with an instrument (column SW-3000G) produced by Toyo Soda Manufacturing Co. Ltd. and marketed under the product code of HLC-803D, at a wavelength of 280 nm.

In the chromatogram of the sample A, only one peak was found. In the chromatogram of the samples B and C, two peaks were found. The compound of the peak which was not found in the sample A but found in the samples B and C was found to have a molecular weight of 94,000, a value suggesting $F(ab')_2$. This fact shows that the unconjugated anti-human IgG•Fab' was reverted by the standing after the dialysis to the anti-human IgG•$F(ab')_2$.

Then, the N-(1-pyrene)maleimide conjugated reaction solution resulting from the reversion of the unaltered anti-human IgG•Fab' to the anti-human IgG•$F(ab')_2$ was applied for purification to a column (2.5 cm in diameter and 100 cm in length) packed Sephacryl S-200, using a 0.02M tris-hydrochloride buffer solution containing 5 mM EDTA and 2.0% sodium chloride (pH 8.0). The eluate was fractionated by a fraction volume of 4 ml and the fractions consequently obtained were measured for absorbance at a wavelength of 280 nm absorbed by $F(ab')_2$ and Fab' and a wavelength of 345 nm absorbed by N-(1-pyrene)maleimide.

The elution pattern at the wavelength of 280 nm showed two peaks similarly to the results of the aforementioned analysis by the high-performance liquid chromatography. The elution pattern at the wavelength of 345 nm showed only one discernible peak. The latter of the two peaks found in the elution pattern of the wavelength of 280 nm and the peak found in the elution pattern of the wavelength of 345 nm were noted to overlap, suggesting that this portion was a fluorescence-labeled Fab' antibody resulting from the conjugation with the fluorescent substance, N-(1-pyrene)maleimide. This fraction was collected and measured for fluorescence (excition wavelength 345 nm and emission wavelength 377 nm) caused by the reaction of N-(1-pyrene)maleimide with a SH group by the use of a spectrofluorophotometer (produced by Hitachi Ltd. and marketed under the product code of "850"). In the measurement, the fraction showed fluorescence of high intensity. The fraction was evaluated with respect to the antibody activity on the human IgG by ELISA (enzyme-linked immunosorbent assay) in accordance with the method introduced by Jean-luc Guesdon et al. [J. Histochem. Cytochem., 27, 1131–1139 (1979)]. In the evaluation, the sample showed strong antibody activity. Thus, this fraction was identified as an N-(1-pyrene)-maleimide labeled Fab'. The portion of the peak which showed absorption only at the wavelength of 280 nm showed the presence of discernible antibody activity and showed the absence of fluorescence of N-(1-pyrene)maleimide. Thus, this fraction was confirmed to be an anti-human IgG•$F(ab')_2$ resulting from the reversion of the unconjugated anti-human IgG•Fab'.

Thus, it was established that the unconjugated anti-human IgG•Fab' and the fluorescence-labeled Fab' could be separated in a refined state from each other.

EXAMPLE 2

A fluorescence-labeled Fab' containing an unconjugated Fab' which had been obtained by causing a fluorescent substance to react with Fab' and purifying the resultant reaction solution by gel filtration while omitting the process of dialysis and standing at rest and the fluorescence-labeled Fab' obtained in Example 1 were tested for intensity of fluorescence and F/P value.

By following the procedure of Example 1, the fluorescence-labeled Fab' obtained without the process of dialysis and standing at rest was obtained by causing the fluorescent substance, N-(1-pyrene)maleimide, to react with Fab', directly purifying the resultant reaction solution with a column packed with Sephacryl S-200 (produced by Pharmacia Fine Chemical Corp.) and collecting the portions showing the absorptions at the wavelengths of 280 nm and 345 nm.

By the use of a spectrofluorophotometer (Hitachi 850), the fluorescence-labeled Fab' containing an unconjugated Fab' which had been obtained without involving the process of dialysis and standing at rest and the fluorescence-labeled Fab' obtained in Example 1 were measured for intensity of fluorescence at a Fab' concentration of 0.1 mg/ml. The intensity of fluorescence of the fluorescence-labeled antibody obtained without the process of dialysis and standing at rest was found to be 605 and that of the fluorescence-labeled Fab' obtained in Example 1 to be 1050.

The F/P value of the fluorescence-labeled Fab' obtained without the process of dialysis and standing at rest and containing an unconjugated Fab' was found to be 1.08 and that of the fluorescence-labeled Fab' obtained in Example 1 to be 1.29. Thus, the fluorescence-labeled Fab' obtained by the process of this invention was found to possess higher intensity of fluorescence and higher F/P.

EXAMPLE 3

A fluorescence-labeled Fab' was prepared by using N-(1-anilinonaphthyl-4)maleimide. By following the procedure of Example 1, 10 mg of an anti-human $\alpha_1$-fetoprotein•$F(ab')_2$ was obtained by digesting an antihuman $\alpha_1$-fetoprotein antiserum IgG fraction (10.1 mg/ml, produced by DAKO) with pepsin and purifying the digestion product by gel filtration. Then this anti-human $\alpha_1$-fetoprotein•$F(ab')_2$ was treated with 2-mercaptoethanol and 10 mg of an anti-human $\alpha_1$-fetoprotein•Fab' was obtained. 1.5 ml of the anti-human $\alpha_1$-fetoprotein•Fab' (6.2 mg/ml) was dialyzed against 0.1M phosphate buffer solution containing 5 mM EDTA (pH 8.0) at 4° C. for 2 hours. 375 µl of a solution of 1.7 mM of N-(1-anilinonaphtyl-4)-maleimide in acetone was added to the dialyzate and then the mixture was incubated under nitrogen at room temperature for one hour.

The resulting reaction solution was dialyzed against 0.1M phosphate buffer solution (pH 7.0), left standing at 4° C. for 48 hours, and purified by gel filtration after the manner of Example 1. 6 mg of a fluorescence-labeled Fab' was obtained. As a control, 8 mg of a fluorescence-labeled Fab' containing an unconjugated Fab' was produced by following the procedure of Example 2. The two samples were measured for the intensity of fluorescence at a Fab' concentration of 0.1 mg/ml. The test for fluorescence was carried out by using a spectrofluorophotometer (Hitachi 850) under the conditions proper for fluorescence measurement of N-(1-anilinonaphthyl- 4)maleimide (excition wavelength 355 nm and emission wavelength 448 nm).

The intensity of fluorescence of the fluorescence-labeled Fab' of the present invention was found to be 1250 and that of the fluorescence-labeled Fab' obtained in Example 2 and consequently containing an unconjugated Fab' was found to be 810. The F/P was 1.41 and 0.99 respectively for the two samples.

What is claimed is:

1. A method for producing fluorescence-labeled Fab' molecules, comprising the steps of:
   (i) reacting a label substance with Fab' molecules, wherein said label substance is a fluorescent molecule or a molecule which, when bound to the -SH group of said Fab', is fluorescent, thereby obtaining a mixture of unreacted Fab' molecules and fluorescence-labeled Fab' molecules in which said fluorescent label is bound to the thiol group of said Fab' molecule;
   (ii) transforming said unreacted Fab' molecules in said mixture to F(ab')$_2$ molecules; and
   (iii) separating said fluorescent-labeled Fab' molecules from said mixture by using the difference in molecular weight between said fluorescence-labeled Fab' molecules and said F(ab')$_2$ molecules.

2. The method of claim 1, wherein said label substance is reacted with said Fab' molecules by dialyzing a Fab' solution against an EDTA-containing buffer solution and subsequently adding said label substance to the resultant dialyzate.

3. The method of claim 2 wherein the concentration of said Fab' molecules in said Fab' solution is in the range of 1 to 20 mg/liter and the concentration of said fluorescent substance is in the range of 0.1 to 1.0 mM.

4. The method of claim 1, wherein said label substance is at least one member selected from the group consisting of 5-(iodoacetamidoethyl)aminonaphthalene-1-sulfonic acid, 5-iodoacetamide fluorescein, N-(1-anilinonaphthyl-4)maleimide, N-(7-dimethylamino-4-methylcumarinyl) maleimide, N-(1-pyrene)maleimide, N-(3-pyrene)maleimide, eosin-5-iodoacetamide, fluorescein mercury acetate, and 2-aminonaphthalene-6-sulfonic acid.

5. The method of claim 4, wherein said label substance is 5-(iodoacetamidoethyl)aminonaphthalene-1-sulfonic acid.

6. The method of claim 4, wherein said label substance is 5-iodoacetamide fluorescein.

7. The method of claim 4, wherein said label substance is N-(1-anilinonaphthyl-4)maleimide.

8. The method of claim 4, wherein said label substance is N-(1-pyrene)maleimide.

9. The method of claim 4, wherein said label N-(7-dimethylamino-4-methyl cumarinyl)maleimide.

10. The method of claim 4, wherein said label substance is N-(3-pyrene)maleimide.

11. The method of claim 4, wherein said label substance is eosin-5-iodoacetamide.

12. The method of claim 4, wherein said label substance is fluorescein mercury acetate.

13. The method of claim 4, wherein said label substance is 2-aminonaphthalene-6-sulfonic acid.

* * * * *